United States Patent
Breitenbach et al.

(10) Patent No.: US 6,627,088 B1
(45) Date of Patent: *Sep. 30, 2003

(54) DEPTH-TYPE FILTER FOR KILLING MICROORGANISMS AND INACTIVATING VIRUSES AND ITS USE

(75) Inventors: Jörg Breitenbach, Mannheim (DE); Bernhard Fussnegger, Kirrweiler (DE); Siegfried Lang, Ludwigshafen (DE); Dietmar Oechsle, Schwäbisch Gmünd (DE)

(73) Assignees: BASF Aktiengesellschaft, Ludwigshafen (DE); Schenk Filterbau GmbH, Waldstetten (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/340,030

(22) Filed: Jun. 28, 1999

Related U.S. Application Data

(62) Division of application No. 08/663,223, filed as application No. PCT/EP94/04092 on Dec. 13, 1994, now Pat. No. 6,083,408.

(30) Foreign Application Priority Data

Dec. 17, 1993 (DE) .......................................... 43 43 226

(51) Int. Cl.⁷ .............................................. B01D 37/00
(52) U.S. Cl. ...................... 210/753; 210/759; 210/764; 210/767; 210/501; 210/504; 210/505; 210/508; 210/645; 424/443; 424/667; 264/DIG. 48
(58) Field of Search ................................. 210/753, 757, 210/758, 764, 501, 503, 504, 505, 508, 645, 759, 767; 424/443, 667; 264/DIG. 48

(56) References Cited

U.S. PATENT DOCUMENTS

| | | | | |
|---|---|---|---|---|
| 5,006,267 A | * | 4/1991 | Vaughn et al. | 210/755 |
| 5,609,864 A | * | 3/1997 | Shanbrom | 424/78.08 |
| 6,045,787 A | * | 4/2000 | Shanbrom | 424/78.24 |
| 6,083,408 A | * | 7/2000 | Breitenbach et al. | 210/753 |
| 6,096,216 A | * | 8/2000 | Shanbrom et al. | 210/638 |
| 6,106,773 A | * | 8/2000 | Miekka et al. | 210/663 |

* cited by examiner

Primary Examiner—Robert J. Popovics
(74) Attorney, Agent, or Firm—Keil & Weinkauf

(57) ABSTRACT

Shaped articles which are suitable as biocidal depth-type filters and consist of fibrous materials and particles, embedded therein, of crosslinked crospovidone-iodine or crospovidone-hydrogen peroxide.

19 Claims, No Drawings

DEPTH-TYPE FILTER FOR KILLING MICROORGANISMS AND INACTIVATING VIRUSES AND ITS USE

CROSS-REFERENCE TO RELATED APPLICATION(S)

This is a Divisional application of Application Ser. No. 08/663,223, filed June 17, 1996, under 35 U.S.C. 371, now U.S. Pat. No. 6,083,408.

Midnight of PCT/EP94/04092 filed Dec. 13, 1994 Depth-type filter for killing microorganisms and inactivating viruses and its use

BRIEF DESCRIPTION OF THE INVENTION

The present invention relates to shaped articles which are suitable as biocidal depth-type filters and consist of fibrous materials and, embedded therein, particles of crospovidone-iodine or crospovidone-hydrogen peroxide. The invention furthermore relates to layer filters containing at least one of the shaped articles as depth-type filter layer. The invention also relates to the use of the shaped articles and of the layer filters for killing microorganisms or inactivating viruses for liquids containing such.

Water, blood or blood products, but also other body fluids or injection solutions, are purified by filtering these products. If it is desired at the same time as the purification also to achieve killing of pathogenic organisms, it is necessary to combine the filtration and purification step with measures which also bring about corresponding inactivation or killing of patho-genic organisms. Various processes and apparatus have been disclosed for this purpose. Thus, WO-92/040 31 discloses that blood, blood derivatives and other body fluids can be purified with soluble PVP-iodine products (povidone-iodine) by killing patho-genic organisms without this harming the substances to be purified. For this purpose, the liquid to be purified is treated with the povidone-iodine, and the liquid treated in this way is then passed through filters. The killed organisms and other impurities then remain in the filter cake, while the liquid which drains off contains the purified products. Although such a process is perfectly effective, it is a multistage-process in which first the dissolved povidone-iodine is brought into contact with the liquid to be purified and subsequently filtration is then carried out. The distinct advantage of this process is that the dissolved povidone remains issolved in the filtrate in this case (even after removal of the iodine) and is virtually impossible to remove again therefrom. The consequence of this is that a product of such a process can no longer be administered directly because it still contains the povidone which does not pass the kidneys. DE-41 19 288 furthermore discloses the purification of pharmaceutical or biological and other liquids by layer filtration. Since such liquids are intended to be free of foreign constituents, especially metal ions, after the purification step, the only substances which can be used for such filters are those with which contamination of the filtrate by metals is not to be expected. This is why DE-41 19 288 proposes the use of filtration aids which have a low metal ion content and are preferably free of metal ions, such as fine highly dispersive polymer granules, micronized celluloses or mixtures of these substances as filtration-active component. Kieselguhr or perlite, which might be effective filtration aids, are unsuitable because of the metal content.

WO 93/06911 describes a process for the filtration of blood using crospovidone-iodine in powder form. This is applied in the form of a bed to a filter. The process requires a crospovidone-iodine with a substantially uniform particle size of 40–150 μm. This is industrially elaborate to produce. In addition, the killed micro-organisms remain in the filtrate and must be removed therefrom. The separation of the cellular components of the blood, which have been filtered off, from the crospovidone-iodine is also elaborate and is difficult to implement on the industrial scale because of the narrow particle size distribution for the particle sizes required for use.

WO 94/00161 describes the treatment of blood or biological tissue with povidone-$H_2O_2$ complexes as biocidal substances, it being possible to use both povidone and crospovidone as basis for the complexes. The biological materials can be treated in an apparatus in which layers of various biocidal substances are arranged one above the other.

DETAILED DESCRIPTION OF THE INVENTION

It was an object of the invention to find depth-type filters consisting of materials such that the purification and, at the same time, the killing of pathogenic organisms and inactivation of viruses in liquids which contain them can be carried out advantageously and without great elaboration. Connected with this object is the use of such a depth-type filter for killing pathogenic organisms in the production of pure water, pharmacological solutions, especially injection solutions, and blood plasma products.

We have found that this object is achieved by the shaped articles which are suitable as biocidal depth-type filters and are defined at the outset, layer filters consisting of one or more shaped articles of this type, and the use thereof for killing micro-organisms and inactivating viruses in liquids containing them.

The shaped articles according to the invention contain as biocidal substance for killing microorganisms or inactivating viruses crospovidone-iodine or crospovidone-hydrogen peroxide (crospovidone-$H_2O_2$). Crospovidone-iodine is the name given to the iodine complex which is based on crosslinked PVP (PVPP, crospovidone) and is used according to the invention.

Free iodine is in equilibrium with the iodine bound in the complex. This proportion as active component is always replenished in a concentration range from 0.5 to 6, preferably 1 to 3, ppm from the iodine pool in the complex.

The iodine can be bound in this complex in various amounts. The commercial products contain from 9.0 to 12.0% by weight of available iodine, but products with an available iodine content of from 1 to 20% by weight are suitable for the present invention. The particle size of the crospovidone-iodine is from 0.5 to 600 μm. Crospovidone-iodine with a particle size distribution from 0.5 to 250 μm is preferably used. The average particle size is from 30 to 40 μm. The specific surface area of the crospovidone-iodine particles is from 0.8 to 6, preferably 1.8 to 2.5, $m^2/g$ [BET method], the apparent density is from 0.1 to 0.35, preferably 0.18 to 0.25, g/ml.

The crospovidone-iodine is present in the shaped articles suitable as depth-type filters in amounts of from 0.5 to 75% by weight, preferably 10 to 50% by weight, particularly preferably 20 to 40% by weight, based on the total weight of the dried shaped article. These amounts depend, on the one hand, on the amount of available iodine present in the crospovidone-iodine and, on the other hand, on the nature of the material to be purified. It is possible to use in a layer filter itself depth-type filters with different amounts of crospovidone-iodine.

In the particulate crosprovidone-$H_2O_2$ which is likewise suitable as biocidal substance, the $H_2O_2$ is likewise bound in the form of a complex to the crosslinked polyvinylpyrrolidone. The particle sizes of the crospovidone-$H_2O_2$ are in the range from 0.5 to 600 µm, preferably from 0.5 to 250 µm. The specific surface area of suitable particles is from 0.8 to 6.0, preferably 1.8 to 2.5, $m^2/g$ (BET method), the apparent density is 0.1 to 0.35, preferably 0.18 to 0.25, g/ml. Complexes of crospovidone and $H_2O_2$ of this type can be prepared by known processes.

The particles of the biocidal substance are embedded in the shaped articles consisting of fibrous materials. The shaped articles consist of fibrous materials which are known for the manufacture of paper and filters, especially cellulose fibers. A suitable fibrous material is, for example, micronized cellulose consisting of pure alpha-cellulose with a residue on ignition not exceeding 0.3%. The length of the fibers in the alpha-cellulose used can be in the range from 10 to 300 µm and, preferably 18 to 200 µm, and an average fiber thickness of from 5 to 30 µm is expedient.

Various additives can be added to adjust the required surface potential. To achieve a positive surface potential it is possible to add a polyamido-amine-epichlorohydrin resin, and for a negative surface potential to add modified galactomannans or poly-acrylamides. It is likewise possible to achieve a negative surface potential by using anionic retention aids.

As substitute for the cellulose or in addition to the cellulose, it is expedient to add polyolefin fibers, for example a poly-ethylene fibrid (PE fibrid). A PE fibrid of this type can have, for example, a fiber length of from 50 to 500 µm and a fiber thickness of from 0.1 to 30 µm. The amount of the added polyethylene fibers is in the range from 1 to 60% by weight based on all the components contained in the particular filter layer (dry weight) and is preferably from 5 to 25 and very preferably about 10% by weight.

The depth-type filters may also consist exclusively of polyethylene fibrid as fibrous materials.

It may furthermore be advantageous to incorporate highly dispersive polymer granules in the filter layer. Particularly suitable for this purpose are, for example, urea-formaldehyde condensates with a primary particle size of from 0.1 to 5 µm and a specific surface area of 20+/−5 $m^2/g$ (BET method) and agglomerates of primary particles in the size from 3 to 300 µm. These polymer granules can be used in amounts of from 1 to 60% by weight, preferably 5 to 20% by weight. It is also possible to add kieselguhr or perlite, in place of or in addition to the polymer granules, within the stated amount of from 1 to 60% by weight, as long as it is ensured that no metal ions are released therefrom or released metal ions are held firmly elsewhere on the filter, or released metal ions do not interfere or, where appropriate, are in fact desired in the filtrate which is to be obtained.

The processes and apparatus used to produce the depth-type filters according to the invention are those used for producing conventional filter materials. For a typical procedure, for example, a pulp which is customary in the papermaking industry is produced in a suitable pulper. This pulp is produced using fibrous materials, that is to say, for example, celluloses or polyolefin fibers which have previously been fibrillated in suitable beater units, for example conical refiners. The substances suitable for the particular filter structure, that is to say, for example, resins which increase the wet strength and/or influence the zeta potential, and the particulate crospovidone-iodine in the suitable amount etc. are then added to the suspension obtained in this way. However, the crospovidone-iodine can also be added to the pulp beforehand.

The aqueous suspension with all the ingredients provided in the formula is then placed on a wire and gently dewatered there so that highly porous structures with a very high turbidity uptake capacity are obtained. This is followed by drying, normally in temperature-controlled multistage dryers, with the drying temperature being controlled so that the temperature-sensitive components present in the mixture are not harmed. In this case, the drying temperature should be, for example, below the softening temperature of polyolefin fibrids present in the filter, normally in the region of 130° C.

The crospovidone-iodine-containing depth-type filter papers generally have a thickness of from 0.1 to 10 mm. The area weight of the individual filter papers can vary within wide ranges and is from 20 $g/m^2$ to 2,500 $g/m^2$. The ash content of the filters varies depending on the nature and amount of the substances present in the filter paper. It is not critical because what matters is not the substances retained in the filter but the purity of the filtrate obtained after the filtration.

The invention also relates to layer filters consisting of the shaped articles according to the invention. Layer filters (filter presses) are known in the prior art. They contain one or more depth-type filter layers through which the liquid to be purified runs, with the layer filters being operated as pressure, suction and hydrostatic filters, depending on requirements. There is normally flow through depth-type filters, it being possible for the layers in the depth-type filter to differ in form by, for example, varying the nature and the density and/or the pore size of the filter layers. The filter layers in the layer filter according to the invention, which is composed of one or more depth-type filter layers or depth-type filter papers, contain preferably 10 to 50% by weight, particularly preferably 20 to 40% by weight, of crospovidone-iodine, which, like the soluble povidone-iodine complexes (based on soluble PVP), has bactericidal, fungicidal and virucidal properties.

On practical use of the depth-type filter according to the invention, the liquid to be purified, especially water, injection solutions or blood plasma products, is placed on the filter. The addition normally takes place from above so that the purified liquid is obtained at the lower end of the depth-type filter. In this case it is expedient to operate with a pressure difference over the entire filter from top to bottom of up to 5 bar. The particles, including bacteria, fungi or viruses, which penetrate into the pores of the layer or of the structure are killed or inactivated by the crospovidone-iodine present in these layers, and the residues are deposited on the inner surface and in the cavities of the layers.

The average residence time of the liquid to be purified on flowing through the depth-type filter is of considerable importance for the mode of action and efficiency of the depth-type filters according to the invention. The contact times are from 0.1 to 5 min, preferably 1 to 2 min. This residence time is influenced, on the one hand, by the depth of the filter bed to be flowed through, and by the internal structure of the individual filter layers. It is desirable for a residence time which is optimal and is adequate to achieve the bactericidal, fungicidal and virucidal properties is set up for a given depth of the depth-type filter. The contact of the liquid to be treated with the crospovidone-iodine complexes or the crospovidone-$H_2O_2$ complexes in the structure of the depth-type filter is, because of the continually changing, usually highly turbulent flow conditions in the pores and channels of the depth-type filter, very intensive and thus the effectiveness is higher, even with very short contact times, than in the processes of the abovementioned prior art. The combination of crospovidone-iodine-containing depth-type filter layers with crospovidone-containing depth-type filter layers (in this sequence) may possibly result in quantitative removal of iodine which is still present in the product. This combination can be incurred, depending on the required contact time, in two different apparatuses successively or by placing the two depth-type filter layers one on top of the other with and without spacer between them.

Depth-type filter layers or filter papers equipped according to the invention with crospovidone-iodine or cropovidone-$H_2O_2$ can also be used in filter presses or be incorporated into filter layer modules or in filter candles in pleated form.

Tests have revealed that a depth-type filter according to the invention can be used effectively to remove pathogenic organisms from water, biological or pharmaceutical or chemical liquids, but especially injection solutions and blood plasma products, and even the residues (debris) of the killed microorganisms are retained in the filter. Since the abovementioned liquids must in any event be subjected to at least one filtration step, the use of a crospovidone-iodine-containing depth-type filter means that the purification can be carried out in a simple, time-saving and cost-saving manner.

The claimed depth-type filters also have the advantage that no povidone is present in the treated filtrate. Where particulate constituents/cell fractions are present in the medium, these result in the filtration without mixing with the aids. Thus, all the steps for elaborate removal of the aids are dispensed with for further processing of the filtration residues.

1. EXAMPLE OF PRODUCTION

A depth-type filter layer for the purification of biological fluids such as, for example, blood plasma fractions is produced as follows:

A pulp mixture of highly bleached sulfite and sulfate pulps from hardwoods and softwoods was beaten in aqueous suspension (pulp) in conical refiners to a degree of beating of about 40°SR (Schopper Riegler). 5 parts by weight of polyethylene fibrid (PE fibrid, type: ESS 21 from Schwarzwalder Textilwerke), 10% by weight of particulate urea/formaldehyde condensate (agglomerates from 6 to 60 mm) and 35% by weight of crospovidone-iodine (particle size distribution 0.5–250 mm) were added to 50 parts by weight of this pulp mixture (based on dry matter). The wet strengthening took place by adding about 0.5% by weight of polyamine/epichlorohydrin resin. The homogeneous suspension of these ingredients was dewatered on a continuously running Fourdrinier wire to about 30–35% DM, with formation of a very porous structure. Subsequently, the wet filter layer is dried at 130 to 140° C. in a continuously operated multistage dryer to a residual moisture <1% and then cut to size. The result is a filter layer which has wet strength and bactericidal, fungicidal and virucidal effects for fine filtration with a pore distribution from 0.05 to 30 μm, with 90% of all pores being from 4 to 6 mm (principle of measurement: Coulter Porometer II) of an area-based weight of 1,200±50 g/m$^2$ and a thickness of 4+0.5 mm.

| Name: | crospovidone-iodine: |
|---|---|
| Nitrogen content | 9.1–11.5% |
| Heavy metal content | ≦10 ppm |
| Loss on drying | ≦6% |
| Ash | <0.3% |
| Available iodine | 9–12.0% |
| Free iodine | 1–3 ppm |
| (10% by weight suspension in $H_2O$) | |

2. EXAMPLE OF USE

Sterilization of Bacteria-containing Media

The depth-type filter layers produced in this way were subjected to validation with the bacterial strain Serratia marcescens. The test method used was the method proposed by the Arbeitskreis Technik/Analytik in der Europaische Fachvereinigung Tiefenfiltration e.V. (method No. 4.2: titer reduction) ("Filtrieren und Separieren" (1994), No. 5, pages 248–250). This test method is based on DIN 58355, Part 3 "Bakterienruickhalteverömbgen von Membranfiltern".

In the tests which were carried out, a filter layer produced in accordance with the example of production was compared with an identical filter layer in which the crospovidone-iodine content was replaced by the pulp mixture, and with a filter layer which was likewise produced identically and in which the crospovidone-iodine content was replaced by a kieselguhr mixture of fines with a permeability of 0.1 Darcy (method 1.3 "Permeabilitäat", Arbeitskreis Technik/Analytik i.d. Europäischen Fachvereinigung Tiefenfiltration e.V.).

These results are reported in LRV values.

(LRV=logarithmic reduction value)

Results:

| | | LRV |
|---|---|---|
| 1. | Depth-type filter with 35% crospovidone-iodine | 10 |
| 2. | Depth-type filter without crospovidone-iodine | 2 |
| 3. | Depth-type filter with 35% kieselguhr mixture | 5 |

This means that the depth-type filter layer with 35% crospovidone-iodine (1) still provides a sterile filtrate with a loading of 108 organisms in 100 ml of unfiltrate per 20 cm$^2$ filter area (Serratia marcescens). With the same loading, the cellulose layer (2) provides a filtrate with 10 organisms in 100 ml and the fine clarification layer (3) with 35% kieselguhr provides a filtrate with 105 organisms per 100 ml. That is to say the crospovidone-iodine-containing depth-type filter layer has a sterilization efficiency which is 5 powers of ten better compared with conventional kieselguhr-containing filter layers.

Inactivation of Viruses

The inactivation of virus suspensions on filtration through depth-type filters according to the invention was determined quantitatively as described below.

The infectiosity of the virus suspensions was measured by determining the cytopathic effect of the viruses on indicator cells in cell cultures before and after the filtration. The reduction in titer indicates the degree of virus inactivation.

Materials:
a) Test viruses
    herpes simplex virus type 1: HSV-A McIntyre strain
    HIV-1: isolate originally called HTLV-IIIB (Gallo-Popovic)
b) Cell cultures for virus stock preparation and titration:
    human fibroblasts α1
    African green monkey kidney cells (GMK)
    MT-2 and MT-4 T-lymphoma cell lines
c) Cell culture media
    Eagle's MEM (Seromed/Biochrom) with fetal calf serum (FCS; 5%), penicillin (100 U/ml) and streptomycin (0.1 mg/ml).
    RPMI medium (Seromed, Biochrom), 10% FCS, antibiotics: penicillin (40 U/ml), streptomycin (0.04 mg/ml)
d) Filtration media
    Eagle's MEM without or with 10% FCS, RPMI, without or with 10% FCS
e) Apparatus
    Filter holder and peristaltic pump supplied by Schenk Filterbau
    Filters produced from cellulose and 20% by weight of 40% by weight crospovidone-iodine and, for comparison, without crosposdone-iodine.

Tests:

Any toxicity of the filtrate for the cell lines used was tested using the 40% and 20% crospovidone-iodine-containing cellulose layers. The filter layer was rinsed with the filtration medium Eagle's MEM without FCS. The first 100 ml filtered (filtrate A) and the next 100 ml (filtrate B) were collected. The cultures were checked for changes in cell growth and cell morphology on the next five days.

No toxic effect on the cells was observed with filtrates A and B from the 20% filter layer. A toxic effect was observed on α1 and GMK cells in the first stage of the serial dilutions with filtrate A from the 40% filter layer. No toxic effect was found with filtrate B. MT-2 cells showed inhibition of growth, but no damage, by filtrate from filters with 40% crospovidone-iodine without FCS at the first titration stage. The corresponding filtrate with FCS did not alter cell growth and cell morphology. Thus, in the inactivation test, the test virus was applied only after 200 or 250 ml of medium had passed through the filters.

In order to rule out that there is inactivation of the virus only in the filtrate after the filtration and not, as desired, in the filter layer, an HSV-1 stock suspension was added to filtrates A and B, and then titration was carried out. The titer was reduced by half a $\log_{10}$ stage with filtrate A, whereas the titer measured with filtrate B was the same as with the appropriately diluted stock suspension. Inactivation by the filtrate was thus ruled out.

It was also tested whether viruses is adsorbed onto the filter layer without crospovidone-iodine. For this, the HSV stock suspension were titrated before and after filtration on a filter layer which contained no crospovidone-iodine.

Main tests:

The filter layer is rinsed with 200 to 250 ml of Eagle's MEM (in tests with HSV-1) or RPMI medium (HIV-1) beforehand. The filtration rate is 16 ml/min. Without interrupting the filtration, 1 ml of the virus suspension is injected in 20 seconds into the liquid flowing onto the filter. Then, 100 ml of filtrate are collected sterile (first filtrate). The inkection and filtration process is repeated twice on the same filter (2nd and 3rd filtrate). The unfiltered virus stock suspension is titrated in parallel with the filtrate: in 24-well plates in $\log_{10}$ dilution stages (4-fold for HSV); HIV was titrated in 96-well plates in three-fold dilution stages and three parallel mixtures. The typically cytopathogenic effect caused by the viruses, or the syncytia formation in the case of HIV, is observed over five days.

The cell culture-infecting units-50 ($TCID_{50}$ [tissue culture infactious dose 50%]) were calculated by a statistical method of Spearman and Kärber. The reduction in the infectiosity is reported in the form of the $\log_{10} TCID_{50}/ml$.

The results of the inactivation tests with HSV-1 are listed in the following Table 1.

The filtrates were titrated as indicated. The virus doses before the filtration were $10_{8.5}$ (test 1) and $10_7$ (test 2) $TCID_{50}/ml$. Test 1 was carried out in the presence of FCS. The reduction in the titer is indicated in logarithms to the base 10.

TABLE 1

| Test No. | 1 | 2 |
| --- | --- | --- |
| Concentration of crospovidone-iodine in % by weight | 20 | 20 |
| FCS | + | − |
| 1 | ≥7 | ≥5.5 |
| 2 | ≥7 | ≥5.5 |
| 3 | 6.5 | ≥5.5 |

The results of the inactivation tests with HIV-1 are listed in Table 2.

The number of infectious units in the filtrate is indicated ($TCID_{50}$).

TABLE 2

| Test No. | 3 | 4 | 5 |
| --- | --- | --- | --- |
| Concentration of crospovidone-iodine in % by weight | 0 | 40 | 40 |
| FCS | + | + | − |
| Filtrate 1 | 120 000 | ≤1 | ≤1 |
| Filtrate 2 | n.d. | ≤1 | ≤1 |
| Filtrate 3 | n.d. | ≤1 | ≤1 | n.d. = not done

This means that $10_5$ infectious units were inactivated by the filtration.

We claim:

1. A shaped article which is suitable for use as a biocidal depth filter and which consists essentially of fibrous materials having incorporated therein biocide particles of crosslinked crospovidone-iodine and a urea/formaldehyde condensation product in form of highly dispersed polymer granules, said shaped article being obtained by a process comprising
    providing an aqueous pulp comprising the fibrous materials, the crospovidone-iodine particles, and the urea/formaldehyde condensate granules,
    spreading the aqueous pulp on a wire and subsequently partially dewatering the spread pulp, and
    drying the partially dewatered pulp, wherein the depth filter has a thickness of from 0.1 to 10 mm and an area weight of from 20 to 3,500 g/m², and comprises the crospovidone-iodine particles in an amount of from 0.5 to 75% by weight, based on the dry weight of the shaped article.

2. The shaped article of claim 1, wherein from 10 to 50% by weight, based on the dry weight of the shaped article, is crospovidone-iodine.

3. The shaped article of claim 1, wherein the crospovidone-iodine particles have a particle size distribution in the range of from 0.5 to 600 μm.

4. The shaped article of claim 1, wherein the average particle size of the crospovidone-iodine particles is from 30 to 40 μm.

5. The shaped article of claim 1, wherein the fibrous components are fibrillated cellulose fibers and/or polyolefin fibers.

6. The shaped article of claim 1, wherein highly dispersed polymer granules and/or kieselguhr and/or perilite are incorporated in the shaped article in an amount of from 1 to 60% by weight based on the dry weight of the shaped article.

7. The shaped article of claim 1, wherein cellulose powder which has been produced by dry milling and has a particle size of from 1 to 100 μm in an amount of from 1 to 60% by weight based on the dry weight of the shaped article is incorporated in the shaped article.

8. A layer filter containing as a depth filter layer at least one shaped article as defined in claim 1.

9. A layer filter as defined in claim 8, containing, before or after the crospovidone-iodine-containing filter layers, other filter layers which contain no crospovidone-iodine.

10. The layer filter of claim 8, wherein the depth filter layers are in the form of layer modules.

11. The layer filter of claim 8, wherein the filter is in the form of a pleated filter candle.

12. The process for purifying a liquid, which process comprises collecting the liquid and filtering it through the shaped article defined in claim 1.

13. The process of claim 12, wherein the liquid to be purified comprises a blood plasma product.

14. The shaped article of claim 1, wherein the fibrous materials are cellulose and/or synthetic fibers.

15. The shaped article of claim 1, wherein the fibrous materials comprise polyethylene fibrid.

16. The shaped article of claim 1, which has an apparent density of from 0.1 to 0.35 g/ml.

17. The shaped article of claim 1, which has an apparent density of from 0.18 to 0.25 g/ml.

18. The shaped article of claim 1, wherein the crospovidone-iodine particles have a specific BET surface area of from 0.8 to 6 $m^2/g$.

19. The shaped article of claim 1, wherein the crospovidone-iodine particles have a specific BET surface area of from 1.8 to 2.5 $m^2/g$.

* * * * *